United States Patent

Andersson et al.

[11] Patent Number: 5,846,264
[45] Date of Patent: Dec. 8, 1998

[54] BACK-UP PULSE GENERATOR

[75] Inventors: Peter Andersson, Stockholm; Nils Holmström, Järfälla; Gunbritt Skog, Göteborg, all of Sweden

[73] Assignee: Pacesetter AB, Solna, Sweden

[21] Appl. No.: 625,252

[22] Filed: Apr. 1, 1996

[30] Foreign Application Priority Data

Mar. 31, 1995 [SE] Sweden ................................ 9501190

[51] Int. Cl.$^6$ .................................................. A61N 1/362
[52] U.S. Cl. ........................................................ 607/28
[58] Field of Search ................................. 607/28, 29, 9

[56] References Cited

U.S. PATENT DOCUMENTS

| | | |
|---|---|---|
| 3,789,854 | 2/1974 | Lee ........................................... 607/29 |
| 3,920,024 | 11/1975 | Bowers . | 
| 4,590,941 | 5/1986 | Saulson et al. ........................... 607/29 |
| 4,693,253 | 9/1987 | Adams . |
| 4,878,497 | 11/1989 | Callaghan et al. . |
| 5,312,448 | 5/1994 | Högnelid et al. . |
| 5,385,575 | 1/1995 | Adams . |
| 5,395,395 | 3/1995 | Hedberg . |
| 5,549,652 | 8/1996 | McClure et al. ........................... 607/28 |

*Primary Examiner*—Scott Getzow
*Attorney, Agent, or Firm*—Hill, Steadman & Simpson

[57] ABSTRACT

A back-up pulse generator for a pacemaker having a first energy storing component for storing energy to be delivered in a stimulation pulse and connectable to means for conducting the stimulation pulse to the heart, the back-up pulse generator including a back-up pulse energy storing component for emitting a back-up pulse after a failure to sense an evoked response from a preceding stimulation pulse. The back-up pulse energy storing component substantially permanently stores energy at a higher voltage than the energy stored in the first energy storing component.

11 Claims, 1 Drawing Sheet

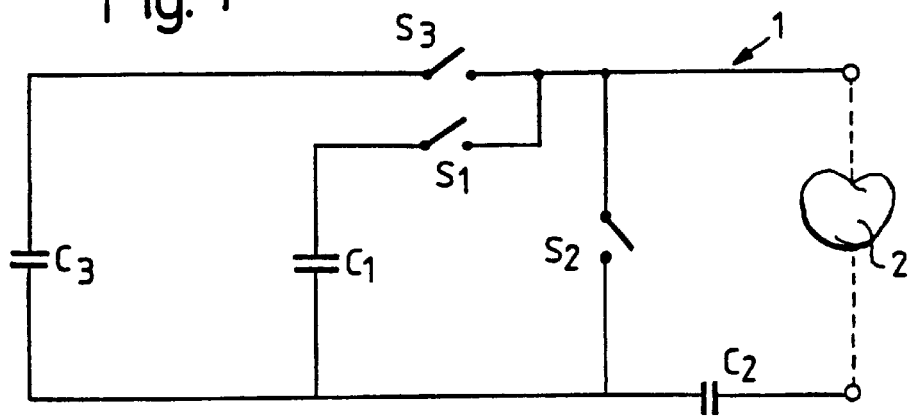
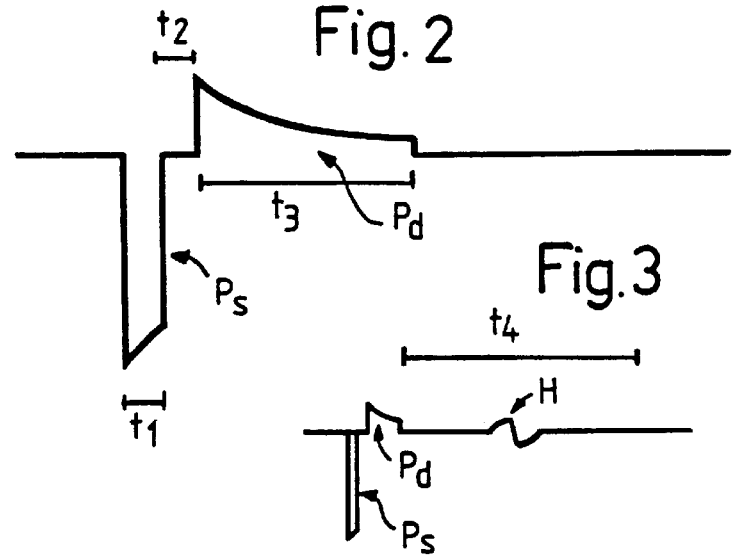
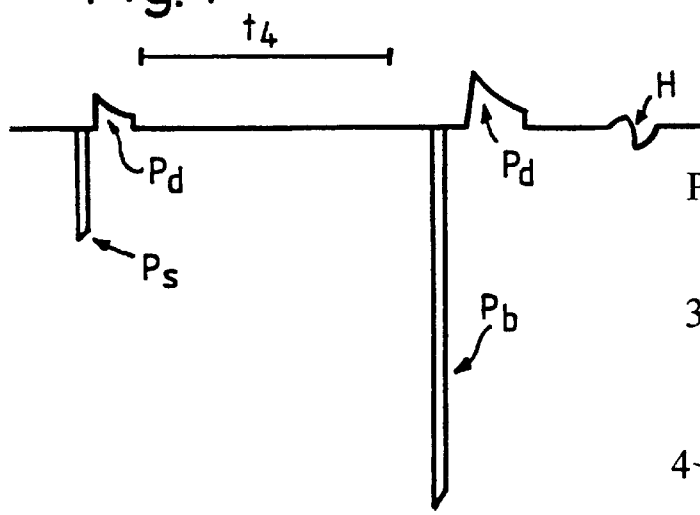
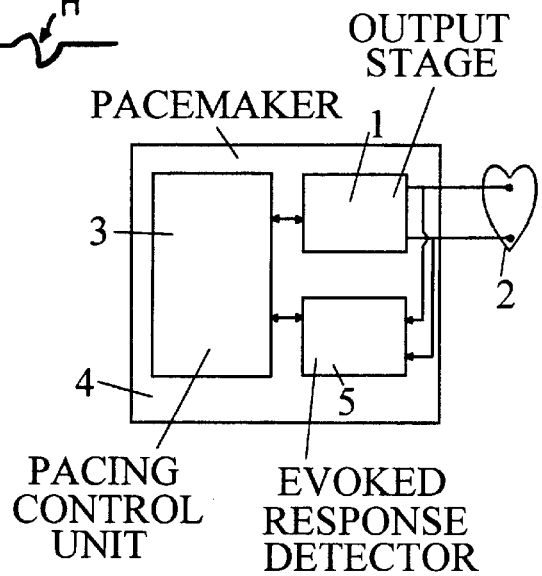

BACK-UP PULSE GENERATOR

BACKGROUND OF THE INVENTION

1. Field of the Invention

The invention relates to back-up pulse generators for use in pacemakers.

2. Description of the Prior Art

Pacemakers stimulate the heart by means of stimulation pulses produced in a pulse generator. In the case of an implantable pacemaker the pulse generator uses energy from the pacemaker battery to charge a stimulation circuit containing energy storing means, usually in the form of one or more capacitors. The charging takes place under the control of a control circuit, which controls the voltage supplied to the energy storing means. Control means also control when the stimulation circuit will discharge a stimulation pulse, the pulse current amplitude and the pulse duration.

In order to extend the battery life of the pacemaker as long as possible, it is desirable to use the lowest possible stimulation pulse output energy which still results in heart capture.

Pacemakers are known which have automatic output regulation, that is, a system for testing for the lowest possible stimulation pulse, output energy which results in heart capture. The energy in a pulse is changed by varying the pulse current and the pulse duration while the pulse initial voltage, that is, the voltage that is stored in the energy storing means, is maintained at a programmable amplitude, for example 1.5 volts. The system has means for detecting heart contractions. In order to use the stimulation electrodes to detect the evoked response, it is customary to emit a compensating pulse after the stimulation pulse, which is transmitted in the opposite direction to the stimulation pulse to neutralize the electrodes. When a stimulation pulse has been discharged to the heart and a successful capture results, the contraction is detected and the system uses an algorithm to decide if the stimulation energy in subsequent pulses is to be reduced. If a pulse does not result in capture, then the algorithm can decide that the stimulation energy in subsequent pulses should be increased.

Some pacemakers have means which not only test for successful capture but also, in the event of loss of capture, are capable of generating a back-up pulse shortly after the failure in order to sense an evoked response from a preceding stimulus. The back-up pulse is supplied from the stimulation circuit, which contains a stimulation capacitor. In order to ensure capture, the energy supplied in the back-up pulse is discharged at the maximum permissible voltage, usually around 4.5 volts. Thus immediately after each stimulation pulse has been discharged, the stimulation capacitor is charged to its maximum voltage of around 4.5 volts, so as to be able to produce a back-up pulse if one is required.

If no back-up pulse is required or if the voltage of the energy remaining in the capacitor after a back-up pulse has been discharged is above the level programmed for the next stimulation pulse, typically 1.5 volts, then some of the stored energy in the capacitor has to be dumped to lower the voltage of the energy stored in the capacitor to the programmed stimulation voltage. This wastes energy which is detrimental to battery life. A pacemaker which can generate a back-up pulse as described above is known from U.S. Pat. No. 4,878,497.

SUMMARY OF THE INVENTION

An object of the invention is to provide a pacemaker wherein a high voltage back-up pulse are generated as well as lower voltage stimulation pulses with a minimum waste of energy.

According to the invention, a dedicated back-up pulse generator is used by the pacemaker to generate the back-up pulse. This back-up pulse generator is maintained charged at the higher back-up pulse voltage so that a source of high voltage energy, as is required for a back-up pulse, is always available. Thus the stimulation capacitor is relieved of the requirement of having to be able to supply a high-voltage back-up pulse, and it is no longer necessary to charge and discharge the stimulation capacitor between stimulation pulses.

DESCRIPTION OF THE DRAWINGS

FIG. 1 is an exemplary circuit of a pacemaker output stage which includes a backup generator in accordance with the invention.

FIG. 2 depicts a stimulation pulse emitted by the circuit of FIG. 1.

FIG. 3 depicts a stimulation pulse followed by a heart contraction as detected by a detection circuit in a pacemaker containing the circuit of FIG. 1.

FIG. 4 depicts a stimulation pulse followed by a back-up pulse emitted by the circuit of FIG. 1.

FIG. 5 is a schematic illustration of a pacemaker including a back-up generator in accordance with the invention.

DESCRIPTION OF THE PREFERRED EMBODIMENTS

A pacemaker 4 is schematically illustrated in FIG. 5, and includes an output stage 1 connected to a heart 2, an evoked response detector 5, also connectable to the heart 2, and a pacing control unit 3 which operates the output stage I and the evoked response detector 5.

In one embodiment of the invention, shown in FIG. 1, the output stage 1 of the pacemaker 4 has, in addition to the usual stimulation capacitor C1 and compensation capacitor C2, at least one back-up pulse capacitor C3. In order to stimulate the heart 2, the stimulation capacitor C1, which typically has a capacitance of 10 microfarads, is charged by a charge pump to a voltage determined by the physician or the manufacturer, which could be, for example, 1.5 volts. When the pulse is to be sent to the heart 2, switch S1 is closed by the pacing control unit 3 and current flows through the output circuit to the heart via the compensation capacitor C2. Compensation capacitor C2 has a capacitance of typically 5 microfarads, and it is charged by the current passing through it.

As shown in FIG. 2, after the programmed pulse duration t1 has been reached, for example 0.5 milliseconds, switch S1 is opened and current ceases to flow. After a delay t2 of typically 1 millisecond, switch S2 is closed which causes the compensation capacitor C2 to discharge a pulse Pd of opposite polarization to that of the stimulation current through the heart for a duration t3 of typically 10 milliseconds.

As shown in FIG. 3, if the stimulation pulse Ps causes the heart 2 to contract, then a signal H corresponding to the contraction will be detected by the contraction (evoked response) detector 5 in the pacemaker well within a period t4 of 45 milliseconds.

If no contraction is sensed in this period, as shown in FIG. 4 then a back-up pulse Pb is required. The back-up pulse capacitor C3 is used to supply the back-up pulse and is kept charged by the pacemaker battery via a charge pump to the programmable maximum permissible voltage, typically 4.5 volts. Back-up pulse capacitor C3 typically can have a capacitance similar to that of the stimulation capacitor C1. When the pacemaker 4 requires a back-up pulse to be sent to the heart 2, the control unit 3 closes the back-up pulse switch S3 which allows the energy stored in the back-up pulse capacitor C3 to start to flow to the heart 2 via compensation capacitor C2. The switch S3 is opened and the flow of energy to the heart 2 is stopped after a predetermined pulse has been sent.

After a delay of typically 1 millisecond, switch S2 is closed which causes the compensation capacitor to discharge a pulse Pd of opposite polarization to that of the back-up current through the heart for a duration of typically 10 milli-seconds. The back-up pulse capacitor C3 is then recharged by the charge pump to the maximum permissible voltage and the stimulation capacitor C1 is charged to the programmed stimulation voltage ready for the next stimulation.

The stimulation capacitor C1 only produces the stimulation pulse and is charged to the programmed voltage, typically 1.5 volts. As the stimulation capacitor C1 is no longer used to produce a back-up pulse, it is no longer necessary to charge it to the maximum voltage after every stimulation pulse; it is just charged to the programmed stimulation voltage. This avoids the requirement to dump energy from the output capacitor before the following stimulation pulse and hence reduces the waste of energy.

In another embodiment of the invention the back-up pulse energy storing means is a battery having a voltage greater than 1.5 volts, preferably 4.5 volts.

In a further embodiment of the invention the back-up pulse energy storing means is a chargeable battery or an accumulator.

In yet another embodiment of the invention the back-up pulse energy storing means is connected in series with the stimulation pulse energy storing means. As examples of this embodiment, the back-up pulse energy storing means can be two capacitors in series each charged with energy at 1.5 volts or one capacitor charged to, for example, 3.0 volts. The stimulation pulse energy storing means could be charged to, for example, 1.5 volts. Thus when a back-up pulse is required the combined back-up pulse voltage from the series-connected back-up pulse and stimulation pulse energy storing means will be the sum of the voltages, for example, 4.5 volts.

Although the examples above have described stimulation pulses which have a voltage of 1.5 volts and back-up pulses with voltages of 4.5 volts, any suitable voltages and pulse durations can be used which fulfill the purpose of pacing the heart. Thus the ratio between the back-up pulse voltage and the stimulation pulses voltage can be any suitable ratio and is not intended to be limited to a ratio of 3:1.

Although modifications and changes may be suggested by those skilled in the art, it is the intention of the inventors to embody within the patent warranted hereon all changes and modifications as reasonably and properly come within the scope of their contribution to the art.

We claim as our invention:

1. A pacemaker comprising first energy storing means for storing energy to be delivered in vivo to a heart in a pacing pulse and connectable to means for conducting the pacing pulse to said heart, detector means for sensing an evoked response of the heart to a pacing pulse, a separate back-up pulse generator having second energy storing means and means for discharging said second energy storing means for emitting a back-up pacing pulse after a failure of said detector means to sense an evoked response from an immediately preceding pacing pulse, said second energy storing means substantially permanently storing energy at a higher voltage than the energy stored in the first energy storing means.

2. A pacemaker as claimed in claim 1, wherein said second energy storing means are coupled in parallel with the first energy storing means.

3. A pacemaker as claimed in claim 1 wherein said second energy storing means comprise at least one capacitor.

4. A pacemaker as claimed in claim 1 wherein said second energy storing means comprise at least one battery.

5. A pacemaker as claimed in claim 1 wherein said second energy storing means contains stored voltage of at least 4.5 volts.

6. A pacemaker as claimed in claim 1 comprising means, when a back-up pacing pulse is required, for coupling the second energy storing means to be at least partially discharged through the means for conducting the pacing pulse to the heart.

7. A back-up pulse generator, for use with a pacemaker having a first energy storing means for storing energy to be delivered to a heart in a pacing pulse and connectable to means for conducting said pacing pulse to the heart, and detector means for sensing an evoked response of the heart to the pacing pulse, said back-up pulse generator comprising second energy storing means and means for discharging said second energy storing means for emitting a back-up pacing pulse after a failure of said detector means to sense an evoked response from an immediately preceding pacing pulse, said second energy storing means substantially permanently storing energy at a higher voltage than the energy stored in the first energy storing means.

8. A back-up pulse generator as claimed in claim 7, wherein said second energy storing means comprise at least one capacitor.

9. A back-up pulse generator as claimed in claim 7, wherein said second energy storing means comprise at least one battery.

10. A back-up pulse generator as claimed in claim 7, wherein said second energy storing means contain stored voltage of at least 4.5 volts.

11. A back-up pulse generator as claimed in claim 7, comprising means, when a back-up pacing pulse is required, for coupling the second energy storing means to be at least partially discharged through the means for conducting the pacing pulse to the heart.

* * * * *